United States Patent
Fernandez Gibello et al.

(10) Patent No.: US 12,127,799 B2
(45) Date of Patent: Oct. 29, 2024

(54) HIGH-VISIBILITY PROTECTED ULTRASOUND NEEDLE FOR CARRYING OUT ULTRASOUND-GUIDED PERCUTANEOUS NEUROMODULATION OR ELECTROLYSIS TECHNIQUES

(71) Applicants: Alejandro Fernandez Gibello, Caceres (ES); Gabriel Camunas Nieves, Caceres (ES); Juan Eloy Fernandez Gibello, Caceres (ES)

(72) Inventors: Alejandro Fernandez Gibello, Caceres (ES); Gabriel Camunas Nieves, Caceres (ES); Juan Eloy Fernandez Gibello, Caceres (ES)

( * ) Notice: Subject to any disclaimer, the term of this patent is extended or adjusted under 35 U.S.C. 154(b) by 985 days.

(21) Appl. No.: 17/253,666

(22) PCT Filed: Jun. 18, 2018

(86) PCT No.: PCT/ES2018/070432
§ 371 (c)(1),
(2) Date: Dec. 18, 2020

(87) PCT Pub. No.: WO2019/243639
PCT Pub. Date: Dec. 26, 2019

(65) Prior Publication Data
US 2021/0259782 A1    Aug. 26, 2021

(51) Int. Cl.
*A61B 34/20* (2016.01)
*A61B 18/14* (2006.01)
(Continued)

(52) U.S. Cl.
CPC .......... *A61B 34/20* (2016.02); *A61B 18/1477* (2013.01); *A61H 39/086* (2013.01);
(Continued)

(58) Field of Classification Search
None
See application file for complete search history.

(56) References Cited

U.S. PATENT DOCUMENTS

| | | | |
|---|---|---|---|
| 4,685,904 A | 8/1987 | Krebs | |
| 2008/0058702 A1* | 3/2008 | Arndt | A61B 17/3401 604/20 |

(Continued)

FOREIGN PATENT DOCUMENTS

| | | |
|---|---|---|
| ES | 2546651 A1 | 11/2016 |
| WO | 1999037223 A1 | 7/1999 |

(Continued)

*Primary Examiner* — Patricia J Park
(74) *Attorney, Agent, or Firm* — Patenting Consulting Group; Roberto J. Rios

(57) ABSTRACT

PROTECTED NEEDLE WITH HIGH ULTRASOUND VISIBILITY FOR PERFORMING ULTRASOUND-GUIDED PERCUTANEOUS ELECTROLYSIS OR NEUROMODULATION TECHNIQUES, consisting of a dry puncture or acupuncture needle formed by a conductive metallic grip (2), coupled to the handle that connects it to the device that generates the electric current to be applied, and a body (3), also conductive and metallic, in the form of a cylindrical, thin and long rod, of variable length among 30, 40, 50, 60, 75 and 100 mm, with the blunt tip (4), where the body (3), and preferably also the grip (2), are both made of galvanized steel with high ultrasound visibility and in that, in addition, said body (3) is provided with a biocompatible electrically insulating protection layer (5) such as a Teflon coating, which covers practically its entire length, except for a working segment (6) of variable length (I) before the blunt tip (4).

13 Claims, 1 Drawing Sheet

(51) Int. Cl.
*A61H 39/08* (2006.01)
*A61N 1/36* (2006.01)
*A61B 17/34* (2006.01)
*A61B 18/00* (2006.01)

(52) U.S. Cl.
CPC ........ *A61N 1/36* (2013.01); *A61B 2017/3413* (2013.01); *A61B 2018/00083* (2013.01); *A61B 2018/00136* (2013.01); *A61B 2034/2063* (2016.02)

(56) References Cited

U.S. PATENT DOCUMENTS

| | | | |
|---|---|---|---|
| 2008/0215039 A1* | 9/2008 | Slatkine | A61M 5/425 606/9 |
| 2012/0095404 A1 | 4/2012 | Massengale et al. | |
| 2014/0121741 A1 | 5/2014 | Bennett et al. | |
| 2016/0331358 A1* | 11/2016 | Gordon | A61B 10/04 |
| 2017/0027632 A1 | 2/2017 | Fernald | |
| 2017/0043063 A1* | 2/2017 | Ayres | A61L 31/18 |

FOREIGN PATENT DOCUMENTS

| | | |
|---|---|---|
| WO | 2008154200 A1 | 12/2008 |
| WO | 2016131999 A1 | 8/2016 |

* cited by examiner

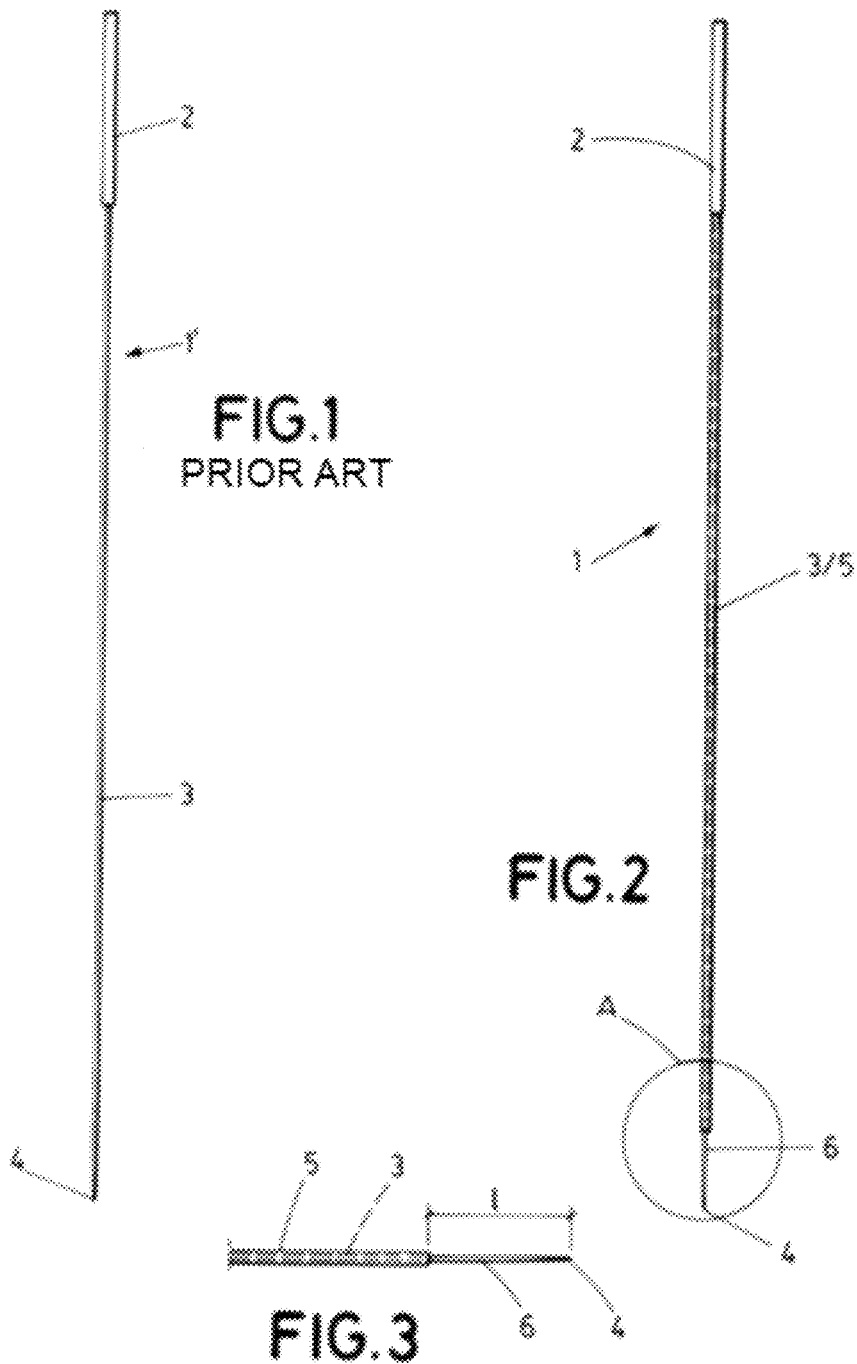

HIGH-VISIBILITY PROTECTED ULTRASOUND NEEDLE FOR CARRYING OUT ULTRASOUND-GUIDED PERCUTANEOUS NEUROMODULATION OR ELECTROLYSIS TECHNIQUES

OBJECT OF THE INVENTION

The invention, as expressed in the wording of the present specification, refers to a protected needle with high ultrasound visibility for performing ultrasound-guided percutaneous electrolysis or neuromodulation techniques that provides, to the function for which it is intended, advantages and novelty characteristics, which are described in detail below, which are an improvement of the current state of the art.

More specifically, the object of the invention is focused on a blunt-tipped acupuncture needle, of the type used in ultrasound-guided percutaneous electrolysis or neuromodulation techniques, based mainly on the passage of galvanic currents through the needle, which presents the innovative particularity of being an electrically protected needle, as it has a protective layer of biocompatible electrically insulating material, preferably constituted by a Teflon coating, which covers practically its entire extension except the working end or tip, and which is also made with a specific material and/or shape that maximize its density and/or minimize ultrasound refraction to provide it with high visibility in the ultrasound machine, whereby its use in these techniques allows the treatment to offer a much higher and efficient precision as well as less painful, thanks to its ability to act only in a localized way on the focus to be treated, normally located under the skin, without injuring other structures or tissues that it passes through and with which the needle comes into contact as it passes to reach said focus and thanks to said greater visibility in the ultrasound machine, the use of which is essential in these techniques.

APPLICATION FIELD OF THE INVENTION

The application field of the present invention is framed within the sector of the industry dedicated to the manufacture of medical devices, apparatuses, and accessories, focusing particularly on the field of accessories for apparatuses and devices to stimulate points of the human body, and more specifically needles for acupuncture techniques with application of galvanic currents for percutaneous electrostimulation.

BACKGROUND OF THE INVENTION

As is known, ultrasound-guided percutaneous electrolysis or neuromodulation techniques are based on the application, at specific points of the body, of galvanic currents and analgesic or neuromodulating currents, through a needle, in order to create a "liquefaction" in a specific area of tissue, to help the repairing/healing process and neuromodulate a structure, normally a nerve, to reduce pain or improve activity thereof.

Specifically, Intratissue Percutaneous Electrolysis (EPI®) or Percutaneous Electrolysis Therapy (EPTER®) are invasive physiotherapy techniques that consist of the ultrasound-guided application of a galvanic current through an acupuncture needle that produces a local inflammatory process allowing phagocytosis and repair of affected soft tissue (tendon, ligament, muscle, etc.). The galvanic electric current and the mechanical stimulus of the needle itself constitute physical agents in the therapeutic field of physiotherapy.

For its part, the ultrasound-guided percutaneous neuromodulation technique is defined as the electrical stimulation through a needle with ultrasound guidance of a peripheral nerve at some point in its path or a muscle at a motor point with a therapeutic purpose. In this case, for safety and to increase effectiveness, it is essential to use an ultrasound machine. The application is based on stimulation with a puncture needle associated with a low or medium frequency electric current, seeking a sensory and/or motor response by stimulating the peripheral nerve, and achieving a motor response by stimulating the motor point.

In both cases, the technique is based on techniques such as segmental dry puncture and neurofunctional acupuncture, whereby the needles used are blunt-tipped needles, without a bevel, since it is not pierced or designed to inject anything, it only has to go through the tissues until the focus to be treated is reached, normally under the skin, at a more or less depth.

The main problem with this type of needles, which are simply formed by a conductive metal body, normally stainless steel, and a somewhat thicker head or grip, generally made of braided steel, for coupling to the handle that connects it to the apparatus or device that generates the current, is that said current is produced and emanates throughout the entire extension of the metal body of the needle, and consequently, the effect of the electric current on the tissues does not only affect the intended focus, but affects all the tissues that the needle passes through and with which it is in contact so that the tip of its end reaches said focus, causing "collateral" damage that, in certain cases, may even be worse than the supposedly beneficial effect intended, since that we can be talking about several centimeters of damaged tissue to attack a subcutaneous internal focus of between one to two millimeters. This, considering that treatments often contemplate the application of these currents at various points during several sessions, supposes a significant volume of unnecessarily damaged tissue.

In addition, a second problem with these treatments is the pain inflicted on the patient, since, although they are low intensity currents, they are still electric currents that, by passing through and attacking the tissues, especially the skin where most of the nerve endings are, cause damage and pain since these are the most pain-sensitive points.

Finally, a third problem with such needles currently used, which are usually made of stainless steel, is the difficulty in the clarity of the images offered through the ultrasound machine, whose use, as mentioned, is essential in the techniques to which it is intended, to achieve precision and efficacy in treatment.

Therefore, it would be desirable to be able to have a new and improved type of needle for use in these techniques that offers protection against the described damage to the tissues, which allows to minimize the pain that the patient has to endure and the damage tissue that the patient receives unnecessarily and, preferably, that also allows a better observation of the images through the ultrasound machine to facilitate the work of the professional when applying the treatment, all of which would have a beneficial effect on its effectiveness, being the development of a needle with these premises the objective of the present invention.

On the other hand, and as a reference to the current state of the art, it should be noted that, at least by the applicant, the existence of any another needle for ultrasound-guided percutaneous electrolysis or neuromodulation techniques that presents technical, structural, and constitutive characteristics equal or similar to those presented here is unknown.

In this sense, it should be mentioned that, as an example of products and/or documents closer to the needle of the invention, the following are known:

Physio Invasiva® Needles, designed for percutaneous electrolysis, dry puncture, and dry acupuncture. They are made of uncoated stainless steel with a headless braided steel grip and a guide tube.

Such a guide tube allows insertion into the skin with less pain, which is useful in dry puncture and percutaneous electrolysis. In the latter case, once the target tissue has been reached with the help of the ultrasound machine, it is attached to the handle to apply the current.

Its main difference with the needle of the present invention is that it is a Teflonless needle, facilitating the calling effect and migration from healthy to degenerated tissue. Damaging in most cases, more tissue than it helps to repair and making it a painful technique.

The non-patent literature document corresponding to the ENRAF NONIUS catalog discloses a 0.30 mm thick Teflonless stainless steel needle for use in percutaneous electrolysis. The difference with the needle of the invention, in addition to the fact that it is Teflonless, it that it is not blunt, nor does it have galvanizing.

Document WO2016131999A1 discloses a device with a Teflon-coated needle, for use in electrostimulation on damaged tissue. However, in addition to being a different device, the described needle comprises two electrodes and is not blunt, since it has a bevel, nor is it galvanized since it is not intended for use with techniques that require ultrasound machine. Specifically, it describes a device intended for the hospital medical sector for diagnosis, induced regeneration in tissues through therapeutic percutaneous electrolysis and focused electrostimulation based on the use of at least one bipolar needle comprising two electrodes in a very reduced area in the external conductor and internal of said bipolar needle, which limits the tissue to be treated in the area of the mouth of the needle without affecting the surrounding healthy tissue, in which the necessary electrical signals are applied to said bipolar needle to diagnose the degree of degeneration and calculate the electrical charge necessary for the treatment of damaged tissue, controlling said current in such a way as to eliminate existing contraindications.

Document WO9937223A1 describes another needle for electrostimulation with Teflon coating. The difference with the needle of the invention, in addition to the fact that it is intended for a quite different current application technique, resides in that it is neither blunt nor galvanized or equipped with a specific shape that increases its visibility in the ultrasound machine, since although its application is focused on intramuscular electrostimulation therapies, it is not intended for ultrasound-guided techniques that use blunt-tipped acupuncture needles.

It should be taken into account that the needle of the present invention is specifically devised and designed for its application in percutaneous electrostimulation techniques that seek to attack a specific point of tissue, located under the skin through the application of low voltage electric current to create the liquefaction of the tissue, through an electrochemical reaction, being the specific structure and configuration that it presents what makes it ideal for it and solving the drawbacks described, and that therefore, said application does not fall within the needles or other instruments that have been used in radio frequency techniques, the purpose of which is to create a thermal injury in a tissue.

Explanation of the Invention

The protected and highly visible ultrasound needle to perform ultrasound-guided percutaneous electrolysis or neuromodulation techniques that the invention proposes is therefore configured as a novelty within its field of application, since according to its implementation and specifically, they are satisfactorily achieved the aforementioned objectives, the characterizing details that make it possible and that distinguish it conveniently included in the final claims that accompany the present description.

More specifically, what the invention proposes, as noted above, is a blunt-tipped acupuncture needle, of the type used in ultrasound-guided percutaneous electrolysis or neuromodulation techniques, mainly based on the passage of galvanic currents through the needle, which has the innovative particularity of being an electrically protected needle, as it has a protective layer of biocompatible electrically insulating material, preferably made up of a Teflon coating, which covers practically its entire extension except the working end or tip, and which also is made with a specific material and/or shape that maximizes its density and/or minimizes ultrasound refraction to give it high visibility in the ultrasound machine, whereby its use in these techniques allows the treatment to offer a much higher and more efficient precision as well as less painful, thanks to its ability to act only in a localized way on the focus to be treated, located under the skin, without damaging other structures or tissues that it passes through and with which the needle comes into contact as it passes to reach said focus, and thanks to this greater visibility in the ultrasound machine, the use of which is essential in these techniques.

Thus, preferably, instead of being a cylindrical stainless steel rod, the needle is made of steel with galvanized treatment, which gives it greater thickness and density, so it is more visible in the ultrasound machine and, alternatively or complementary, at least the active end thereof, has a non-cylindrical shape, for example spiral, flat, quadrangular, triangular or other that provides a greater bounce surface and less refraction in the incidence waves from the ultrasound machine, whereby its visibility in it is increased.

It should be noted that the end that remains uncovered with the electrically insulating layer can be of variable length, depending on each application, preferably comprising a range from 0.5 mm to 1 cm.

The needle of the invention is therefore a dry puncture or acupuncture needle with a blunt tip, without bevel or hollow or provided with electrodes, which has a Teflon-coated protection to be electrically isolated in its path, that is, in most of the length of the metal rod that constitutes the body thereof so that the effect of the current only occurs at the tip, where said protection no longer covers the rod, and thereby the structures to be injured are not injured.

The needle is a needle of the type known as dry puncture or acupuncture, preferably 0.30 mm thick, although it can vary, and also of variable length, preferably 30, 40, 50, 60, 75 and 100 mm, distinguishing in that the Teflon-coated insulating protection layer and in that it has a different type of galvanization and processing that allows it to be seen better in the ultrasound machine.

The problem with the current needle is that as it is not Teflon-coated, it causes the current to create an electrochemical reaction, which damages the entire path and it does not make sense that if the ultrasound machine is used to focus the treatment to a focus of 1-2 mm, then it damages all the tissue where the needle passes, which may be more than 5 cm.

Optionally, the needle of the invention is used inserted into a guide tube to achieve a better perforation of the skin and less pain for the patient, the pressure exerted by the guide tube creates an effect known as "gate control", whereby, when noticing a pressure stimulus, the nerve transmits painful stimuli worse.

The described protected and high ultrasound visibility needle to perform ultrasound-guided percutaneous electrolysis or neuromodulation techniques represents, therefore, an innovation with structural and constitutive characteristics unknown until now, reasons that together with its practical utility, provide it with sufficient basis to obtain the privilege of exclusivity that is requested.

DESCRIPTION OF THE DRAWINGS

In order to complete the description being made and to ease a better understanding of the characteristics of the invention, we attach to the present specification, making part of the same, a layout where, with an illustrative non limitative character, the following has been represented:

FIG. 1—Shows an elevation view of a needle to perform ultrasound-guided percutaneous electrolysis or neuromodulation techniques, according to the current technique, with its general configuration and the parts it comprises being appreciated, that is, the grip for coupling to the handle and the body in the form of a cylindrical, thin, and long rod with a blunt tip, without insulating protection and made of stainless steel.

FIG. 2—Shows an elevation view of the protected needle with high ultrasound visibility to perform ultrasound-guided percutaneous electrolysis or neuromodulation techniques, object of the invention, with its configuration and main parts being appreciated, that is, the grip for coupling to the handle and the body in the form of a cylindrical, thin, and long rod with a blunt tip, provided with its biocompatible electrically insulating protection layer.

FIG. 3—Shows an enlarged view of detail A, indicated in FIG. 2, centered on the distal end with blunt tip of the needle, of the invention, with the segment thereof that remains free of the biocompatible electrically insulating protection layer being appreciated.

PREFERRED EMBODIMENT OF THE INVENTION

In light of the mentioned figures, and according to the numbering taken on them, can be seen in them an example of non-limiting realization of the recommended protected needle with high ultrasound visibility for performing ultrasound-guided percutaneous electrolysis or neuromodulation techniques, which includes the parts and elements indicated and described in detail below.

Thus, as can be seen in FIG. 1, according to the prior art, the needles (1') to perform ultrasound-guided percutaneous electrolysis or neuromodulation techniques are dry puncture or acupuncture needles formed by a conductive metallic grip (2), coupled to the handle that connects it to the device that generates the electric current to be applied (element not shown) and a body (3), also conductive metallic, in the form of a fully cylindrical, thin and long rod, of variable length among 30, 40, 50 60, 75 and 100 mm, with the blunt tip (4), both made of stainless steel.

And, as can be seen in FIGS. 2 and 3, the protected needle with high ultrasound visibility (1) of the invention, also consisting of a dry puncture or acupuncture needle formed by a conductive metallic grip (2), coupled to the handle that connects it to the device that generates the electric current to be applied and a body (3), also conductive metallic, in the form of a long thin rod, of variable length among 30, 40, 50, 60, 75 and 100 mm, and with the blunt tip (4), which is distinguished in that at least the body (3), and preferably also the grip (2), are made of a material that maximizes its density and/or a shape that minimizes refraction ultrasound to give it high ultrasound visibility, and in that, in addition, said body (3) is provided with a biocompatible electrically insulating protection layer (5) that covers practically its entire length, except for a working segment (6) of variable length (I) before the blunt tip (4).

Preferably, said material that maximizes its density to increase its visibility in the ultrasound machine, at least in the body (3) is galvanized steel, and preferably the shape it presents to minimize ultrasound refraction, at least at the working end (6) is a non-cylindrical shape of the rod that forms said body (3) of the needle, being, for example, spiral, flat, quadrangular, triangular or other that, in any case, provides a greater bounce surface and less refraction than a surface cylindrical to the incidence of the ultrasound waves, whereby its visibility in it is increased, being able to comprise both characteristics at the same time, that is, to be made of galvanized steel and present, at least in the working segment (6), said non-cylindrical shape.

In any case, preferably, the biocompatible electrically insulating protection layer (5) is constituted by a Teflon coating. And, preferably said working segment (6) that does not cover the protection layer (5) has a length (I) between 0.1 mm and 10 mm.

Optionally, the needle (1) of the invention allows an insertion into the skin with less pain. Extremely useful in dry puncture and percutaneous electrolysis. In the latter case, once the target tissue is reached with the help of the ultrasound machine, it is attached to the handle. The guide tube is still useful, so that it pierces the skin better and that the patient feels less pain. In our case, we will also use it (they are needles that bend easily and, in some cases, do not pierce the skin well).

Having sufficiently described the nature of the present invention, as well as the way of putting it into practice, it is not considered necessary to make a more extensive explanation thereof in order that any expert in this area will understand its scope and the advantages that can be derived from it, making known that, within reason it could be put into practice in other embodiments differing in detail from that indicated by way of example, and with which it will also achieve the protection that is sought provided that its fundamental principle is not altered, changed or modified.

The invention claimed is:

1. Protected needle with high ultrasound visibility for performing ultrasound-guided percutaneous electrolysis or neuromodulation techniques consisting of a dry puncture or acupuncture needle formed by a conductive metallic grip (2) coupled to a handle that connects it to a device that generates an electric current to be applied, and a conductive and metallic body (3) in the form of a cylindrical, thin and long rod having a length variable among 30, 40, 50, 60, 75 and 100 mm, with a blunt tip (4), said protected needle comprising:

said body (3) being made of galvanized steel for maximizing a density of said body (3) and being shaped at least partially non-cylindrical for minimizing an ultrasound refraction that provides high ultrasound visibility and said grip (2) being made of galvanized steel that maximize a density of said grip (2) in order to provide high ultrasound visibility of said needle; and a biocompatible electrically insulating protection layer (5) covering a length of the body (3) except a working segment (6) of variable length (1) provided before the blunt tip (4).

2. Protected needle according to claim 1, wherein said biocompatible electrically insulating protection layer (5) comprises a Teflon coating.

3. Protected needle according to claim 1, wherein the working segment (6) has a length (I) between 0.1 mm and 10 mm.

4. Protected needle according to claim 1, wherein the body (3) has a non-cylindrical shape only in the working segment (6).

5. Protected needle according to claim 1, wherein the non-cylindrical shape of the body (3) has a spiral, a flat, a quadrangular, or a triangular shape that increases a bounce surface for the ultrasound waves.

6. Protected needle with high ultrasound visibility for performing ultrasound-guided percutaneous electrolysis or neuromodulation techniques consisting of a dry puncture or acupuncture needle formed by a conductive metallic grip (2) coupled to a handle that connects it to a device that generates an electric current to be applied, and a conductive and metallic body (3) in the form of a cylindrical, thin and long rod having a length variable among 30, 40, 50, 60, 75 and 100 mm, with a blunt tip (4), said protected needle comprising:
   said body (3) being made of galvanized steel for maximizing a density of said body (3) and said grip (2) being made of galvanized steel that maximize a density of said grip (2) in order to provide high ultrasound visibility of said needle; and
   a biocompatible electrically insulating protection layer (5) covering a length of the body (3) except a working segment (6) of variable length (1) provided before the blunt tip (4).

7. Protected needle according to claim 6, wherein said biocompatible electrically insulating protection layer (5) comprises a Teflon coating.

8. Protected needle according to claim 6, wherein the working segment (6) has a length (I) between 0.1 mm and 10 mm.

9. Protected needle with high ultrasound visibility for performing ultrasound-guided percutaneous electrolysis or neuromodulation techniques consisting of a dry puncture or acupuncture needle formed by a conductive metallic grip (2) coupled to a handle that connects it to a device that generates an electric current to be applied, and a conductive and metallic body (3) in the form of a cylindrical, thin and long rod having a length variable among 30, 40, 50, 60, 75 and 100 mm, with a blunt tip (4), said protected needle comprising:
   said body (3) being shaped at least partially non-cylindrical for minimizing an ultrasound refraction that provides high ultrasound visibility and said grip (2) being made of galvanized steel that maximize a density of said grip (2) in order to provide high ultrasound visibility of said needle; and
   a biocompatible electrically insulating protection layer (5) covering a length of the body (3) except a working segment (6) of variable length (1) provided before the blunt tip (4).

10. Protected needle according to claim 9, wherein said biocompatible electrically insulating protection layer (5) comprises a Teflon coating.

11. Protected needle according to claim 9, wherein the working segment (6) has a length (I) between 0.1 mm and 10 mm.

12. Protected needle according to claim 9, wherein the body (3) has a non-cylindrical shape only in the working segment (6).

13. Protected needle according to claim 9, wherein the non-cylindrical shape of the body (3) has a spiral, a flat, a quadrangular, or a triangular shape that increases a bounce surface for the ultrasound waves.

* * * * *